(12) United States Patent
Tsuchiya et al.

(10) Patent No.: US 9,057,711 B2
(45) Date of Patent: Jun. 16, 2015

(54) INSPECTION APPARATUS AND METHOD

(75) Inventors: Hideo Tsuchiya, Tokyo (JP); Takafumi Inoue, Kanagawa (JP); Nobutaka Kikuiri, Tokyo (JP)

(73) Assignee: NuFlare Technology, Inc., Numazu-shi (JP)

( * ) Notice: Subject to any disclaimer, the term of this patent is extended or adjusted under 35 U.S.C. 154(b) by 800 days.

(21) Appl. No.: 13/307,389

(22) Filed: Nov. 30, 2011

(65) Prior Publication Data

US 2012/0140060 A1 Jun. 7, 2012

(30) Foreign Application Priority Data

Dec. 6, 2010 (JP) ................................. 2010-272014

(51) Int. Cl.
*H04N 7/18* (2006.01)
*G01N 21/956* (2006.01)
*G01N 21/88* (2006.01)

(52) U.S. Cl.
CPC ...... *G01N 21/95607* (2013.01); *G01N 21/8851* (2013.01); *G01N 2021/95615* (2013.01); *G01N 2021/95676* (2013.01)

(58) Field of Classification Search
CPC .............................................. G01N 21/95607
USPC ....................................................... 348/126
See application file for complete search history.

(56) References Cited

U.S. PATENT DOCUMENTS

| | | | |
|---|---|---|---|
| 5,305,391 A * | 4/1994 | Gomibuchi | 382/142 |
| 6,888,959 B2 * | 5/2005 | Hamamatsu et al. | 382/149 |
| 7,116,816 B2 * | 10/2006 | Tanaka et al. | 382/149 |
| 7,523,027 B2 | 4/2009 | Chang et al. | |
| 7,664,308 B2 * | 2/2010 | Isomura | 382/144 |
| 8,103,087 B2 * | 1/2012 | Maeda et al. | 382/149 |
| 8,139,841 B2 * | 3/2012 | Shibuya et al. | 382/141 |

(Continued)

FOREIGN PATENT DOCUMENTS

| | | |
|---|---|---|
| EP | 1 012 779 B1 | 10/2009 |
| JP | 2001-516898 | 10/2001 |

(Continued)

OTHER PUBLICATIONS

Japanese Office Action issued Jan. 7, 2014, in Japan Patent Application No. 2010-272014 (with English translation).

(Continued)

*Primary Examiner* — William C Vaughn, Jr.
*Assistant Examiner* — Luis M Perez
(74) *Attorney, Agent, or Firm* — Oblon, McClelland, Maier & Neustadt, L.L.P.

(57) ABSTRACT

An inspection apparatus and method, which can perform defect determination and estimate a defect on a mask and the resultant influence on a wafer. Each of the transfer images is reviewed in order of following (1) to (3):

(1) when the degree of defect identified in the first comparing unit is at or exceeding a third threshold and an error ratio corresponding to the defect is at or exceeding a fourth threshold;

(2) when the degree of a defect identified in the first comparing unit is less than the third threshold, and an error ratio corresponding to the defect is at or exceeding a fourth threshold; and (3) when the degree of a defect identified in the first comparing unit is at or exceeding a third threshold, and an error ratio corresponding to the defect is less than the fourth threshold.

6 Claims, 13 Drawing Sheets

(56) References Cited

U.S. PATENT DOCUMENTS

| | | | |
|---|---|---|---|
| 8,548,223 B2* | 10/2013 | Inoue et al. | 382/145 |
| 2005/0076322 A1 | 4/2005 | Ye et al. | |
| 2006/0239535 A1 | 10/2006 | Takada et al. | |
| 2011/0044528 A1 | 2/2011 | Tsuchiya et al. | |
| 2011/0044529 A1 | 2/2011 | Tsuchiya et al. | |
| 2011/0083113 A1 | 4/2011 | Ye et al. | |
| 2012/0128230 A1* | 5/2012 | Maeda et al. | 382/145 |

FOREIGN PATENT DOCUMENTS

| | | |
|---|---|---|
| JP | 2007-192652 | 8/2007 |
| JP | 2008-112178 | 5/2008 |
| JP | 2009-105430 | 5/2009 |

OTHER PUBLICATIONS

U.S. Appl. No. 13/768,392, filed Feb. 15, 2013, Inoue, et al.
U.S. Appl. No. 13/792,364, filed Mar. 11, 2013, Inoue, et al.
U.S. Appl. No. 13/705,663, filed Dec. 5, 2012, Tsuchiya, et al.
Carl Hess, et at "A Novel Approach: High Resolution Inspection with Wafer Plane Defect Detection", Proc. of SPIE, vol. 7028, 2008, pp. 70281F-1-70281F-11.
Dan Rost, et al., "Qualification of Aerial Image 193nm Inspection Tool for All Masks and All Proces Steps", Proc. of SPIE vol. 7028, 2008, pp. 70282Q-1-70282Q-12.

\* cited by examiner

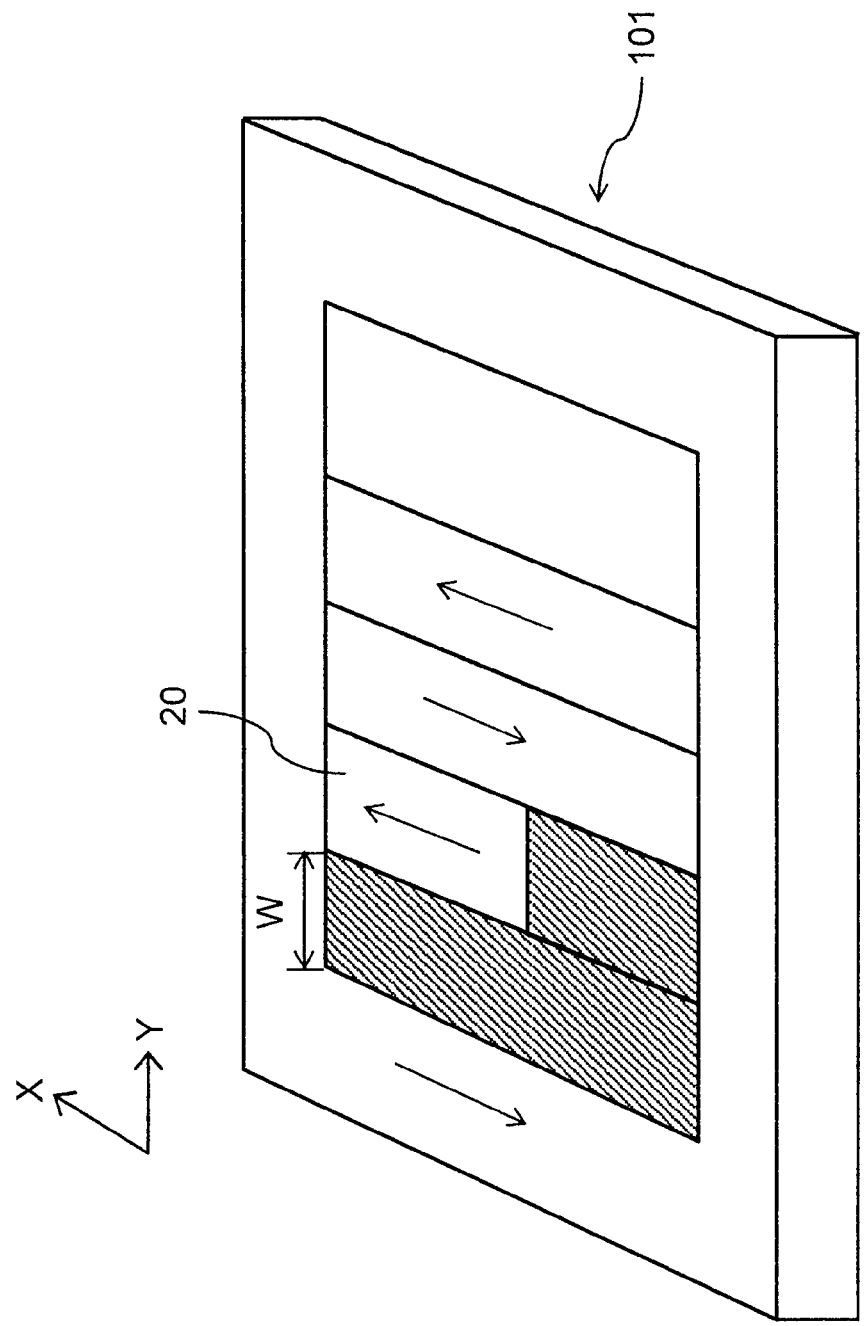

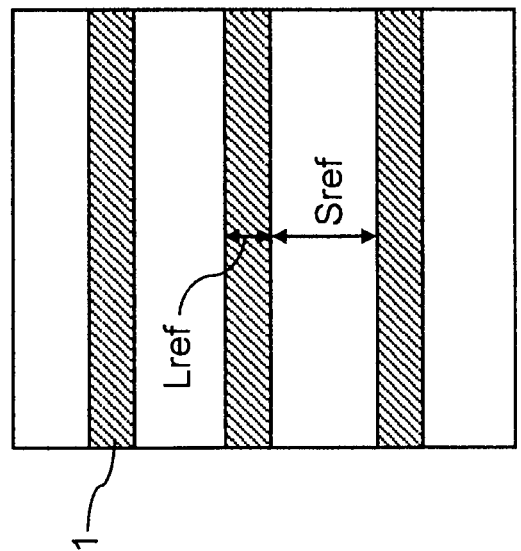
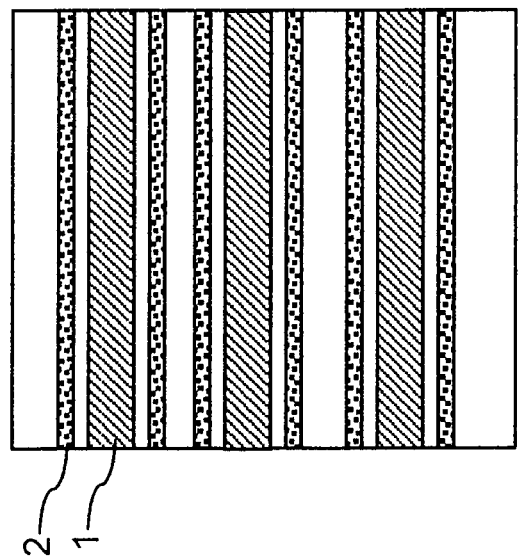

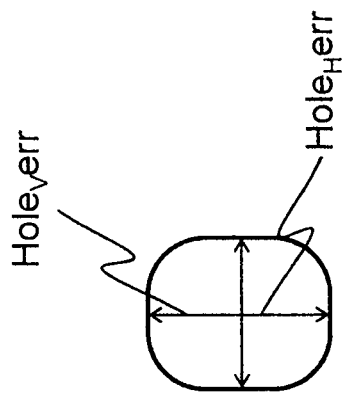
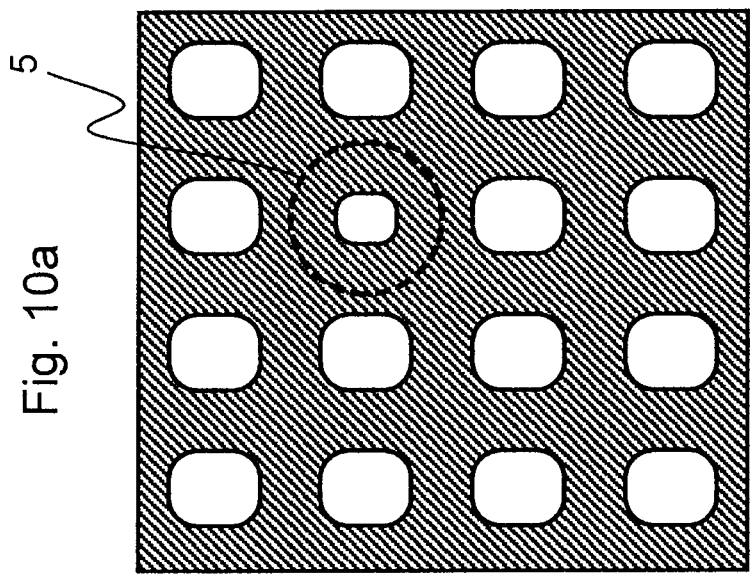

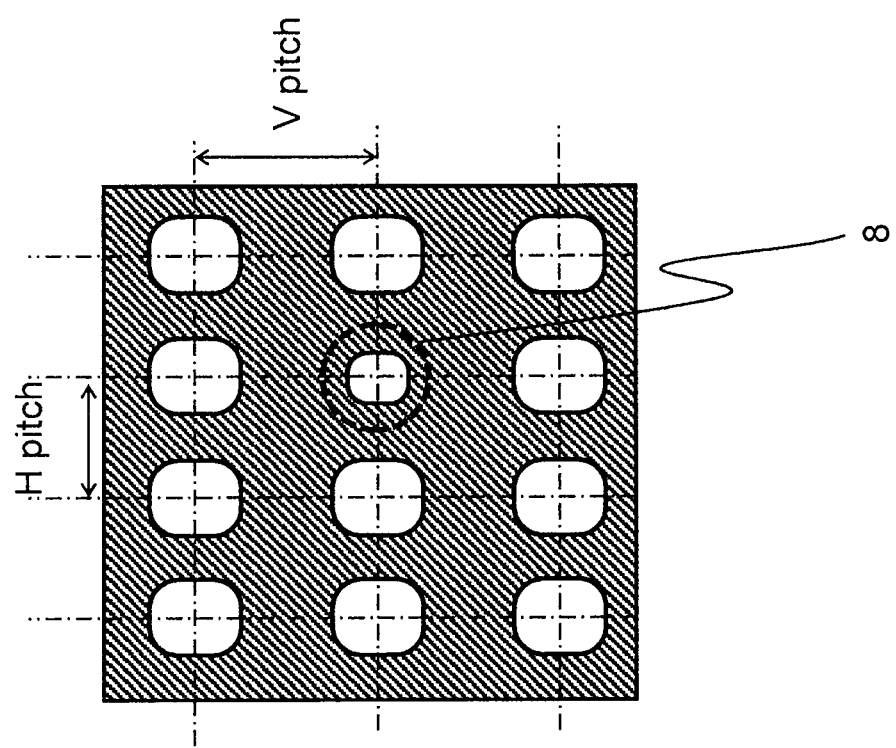

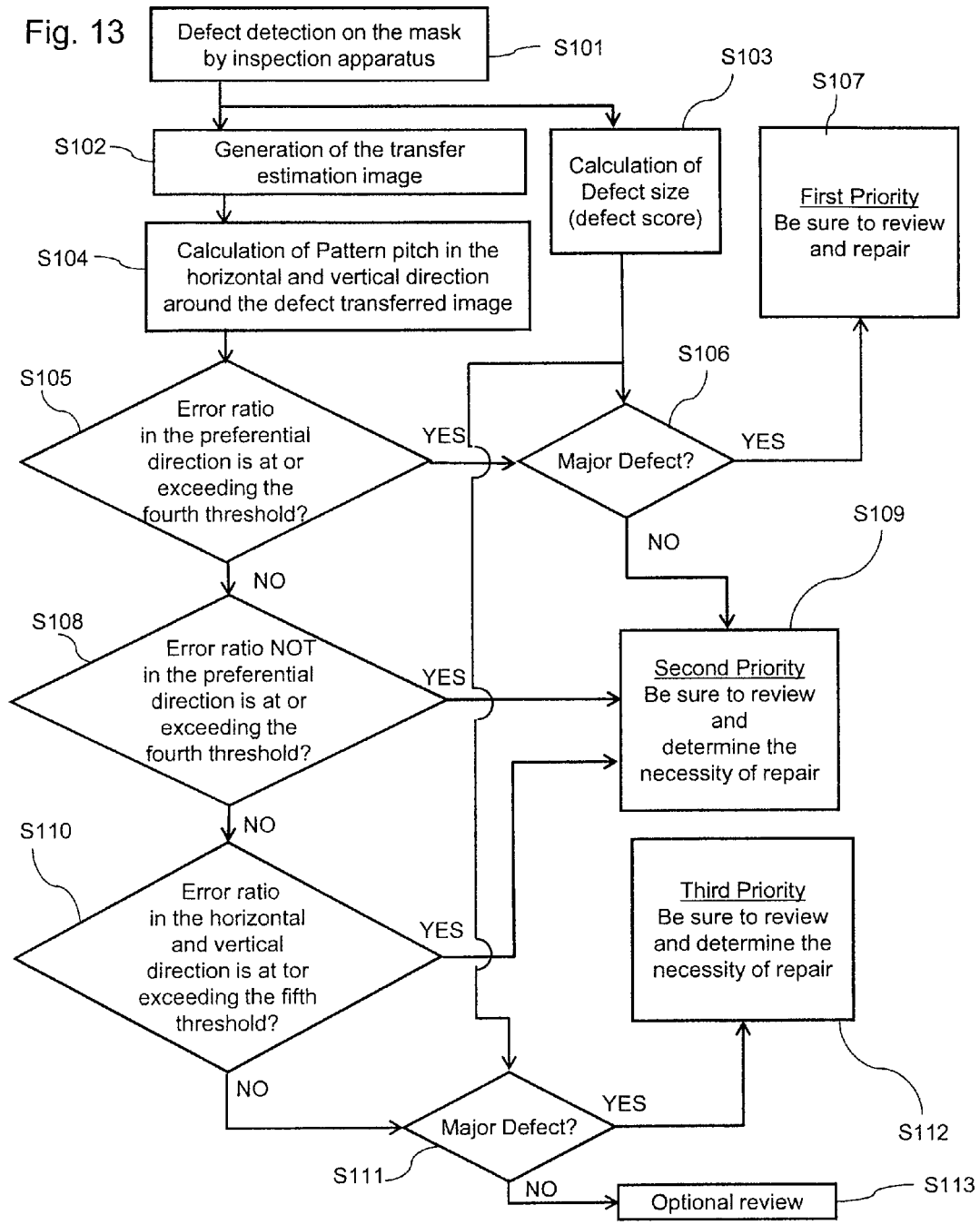

INSPECTION APPARATUS AND METHOD

CROSS-REFERENCE TO THE RELATED APPLICATION

The entire disclosure of the Japanese Patent Application No. 2010-272014, filed on Dec. 6, 2010 including specification, claims, drawings, and summary, on which the Convention priority of the present application is based, are incorporated herein in its entirety.

FIELD OF THE INVENTION

The present invention relates to an inspection apparatus and inspection method used to detect defects of a pattern formed on an object to be inspected such as a mask.

BACKGROUND

In recent years, as the levels of integration and capacity of large scale integrated circuits (LSIs) have increased, there has been a need to continue to reduce the width of the circuit patterns of semiconductor devices. Semiconductor devices are manufactured by a reduced projection exposure apparatus called a "stepper" using original artwork patterns with a circuit pattern formed thereon, these are called masks or reticles (hereinafter referred to collectively as masks). Specifically, a pattern on a mask is transferred to the wafer by exposure to light, thereby forming circuits on to a wafer. Masks used to transfer such fine circuit patterns to the wafer are manufactured by electron beam writing apparatuses, which can write micropatterns. Further, effort has been made to develop a laser beam writing apparatus, which uses a laser beam for writing. It should be noted that electron beam apparatuses are also used to directly write a circuit pattern on a wafer.

Incidentally, since the cost to manufacture LSIs is very high, an increase in yield is required to make the manufacturing economically feasible. Meanwhile, recent representative logic devices require a pattern having a line width of several ten nano-meters. Major factors that reduce the yield include a mask containing a pattern defect and a variation in conditions of the exposure transfer. In the prior art, with the miniaturization of an LSI pattern dimension to be formed on a semiconductor wafer, mask dimensional accuracy has been improved, by the variation margin of process terms and conditions having been absorbed. Therefore, in the mask inspection, the dimension of the pattern defect is miniaturized, and a positional error of an extremely small pattern is required to be inspected. Therefore, high inspection accuracy is required of inspection apparatuses for detecting defects of masks used in LSI manufacture.

One of the factors that allow miniaturization of a mask pattern is the application of Resolution Enhancement Technology (herein after referred to as RET). In the RET technique, an auxiliary pattern referred to as an assist pattern is disposed on the side of a main pattern, whereby the formability of the main pattern is improved. Although the auxiliary pattern is not part of a transfer image, light energy entering a region of the main pattern is secured by the provision of the auxiliary pattern. In a mask inspection apparatus, such a defect of the assist pattern can also be detected.

There are two known mask defect detecting methods: the die-to-die inspection method and the die-to-database inspection method. The die-to-die inspection method is used when the mask to be inspected has thereon a plurality of identical chip patterns, or a plurality of chip patterns each including an identical pattern segment. In this method, these identical chip patterns or identical pattern segments, which are to be printed to the wafer, are compared to each other. This method permits accurate inspection using a relatively simple system configuration, since patterns on the same mask are directly compared to each other. However, this method cannot detect a defect common to both compared patterns. In the die-to-database inspection method, on the other hand, an actual pattern on a mask is compared to reference data generated from the design pattern data that was used to manufacture the mask. Thus, this method allows exact comparison of the pattern with the design pattern data, although the required system size is large since the method requires a processing system for generating a reference image. There is no choice but to use this inspection method when the mask to be inspected has only one chip pattern to be transferred to the wafer.

In die-to-die inspection, light is emitted from a light source, and the mask to be inspected is irradiated with this light through an optical system. The mask is mounted on a table, and this table is moved so that the emitted beam of light scans the surface of the mask. Light transmitted through or reflected from the mask reaches an image sensor, thereby forming an image thereon. The optical image thus formed on the image sensor is sent to a comparing unit as measurement data. The comparing unit compares the measurement data with reference data in accordance with an appropriate algorithm, and if they are not identical, the mask is determined to have a defect (see Patent Document 1).

In the prior art inspection apparatus, a mask pattern image obtained by imaging an optical image by an image sensor is determined to be correct. However, with the recent miniaturization of a device pattern on a mask, it is difficult to distinguish a difference between a shape defect of a pattern and a potentially existing shape error of a pattern. Further, the required accuracy of a linewidth or pattern of a mask increases, whereby determination as to whether or not there is a defect is difficult if the only comparison is between generated reference data based on design pattern data and a pattern image taken by an inspection apparatus.

In order to address this problem, a defect determining method has been proposed which uses the shape of the mask pattern printed on the wafer. Non-Patent Document 1 shows a method of acquiring an inspected mask image by a CCD (Charge Coupled Device), using a high-resolution optical system and a method of obtaining a wafer aerial image by using a low-resolution optical system (see, FIG. 1). In the former method, the mask image of the inspected pattern and the reference pattern is acquired by the high-resolution optical system. A wafer transfer image is estimated from the mask image through the process of FIG. 2. Thereafter, the wafer transfer images are compared with each other and defect determination is performed. Meanwhile, in the latter method, the wafer transfer image is directly collected by an optical wafer transfer device. In these methods, an image to be transferred onto a wafer is predicted, and the defect determination is performed based on the image. The latter method is also described in Non-Patent Document 2 (see, FIG. 3 and the bottom of page 3).

When a plurality of fractures and taper shaped defects occur in an assist pattern corresponding to a certain part of the main pattern on a mask, the shape of the main pattern in an estimated wafer transfer image should be in such a state that a dimensional error such as constriction of the line width occurs. That is to say, according to a determination method based on a transfer image, it can be predicted that the shape defect of a mask makes the transfer image incorrect. However, in this case, there is a problem that it cannot be indicated which of the defect portions in the assist pattern, that is, which of a plurality of fracture portions causes the constriction of the line width in the main pattern, or which combination of the plurality of fracture portions causes the constriction of the line width in the main pattern.

Patent Document 2 discloses a method for simulating a lithographic design comprised of a number of polygons arranged in a predetermined configuration. Specifically, referring to FIG. 4 of this publication, an aerial image is generated using a bitmap image available from the polygon design database (box 126), and resist modeling or simulation is performed using this aerial image (box 128). FIG. 7 shows a technique of estimating a wafer pattern aerial image by simulation of an image from a mask inspection apparatus. This technique indicates whether a wafer aerial image or a wafer image, obtained through a wafer generation process such as reaction of photoresist by light exposure, is correct.

Further, Patent Document 3 states as follows: "In any mask inspection system, the important decision to make is whether a defect will 'print' on the underlying photoresist in a lithography process under specified conditions.

If a mask defect does not print or have other effect on the lithography process, then the mask with the defect can still be used to provide acceptable lithography results. Therefore, one can avoid the expense in time and cost of repairing and/or replacing masks whose defects do not print."

Patent Document 3 discloses a method of acquiring a defect area image including an image of a portion of a mask and generating a simulated image. This simulated image includes a simulation of an image which would be printed on the wafer.

As described above, according to the prior art inspection apparatus, an estimated transfer image that would be transferred to the wafer including defects acquired by the inspection apparatus can be generated.

[Patent Document 1] Japanese laid-open Patent publication No. 2008-112178

[Patent Document 2] Japanese laid-open Patent publication No. 2009-105430

[Patent Document 3] Published Japanese translation of PCT application No. 2001-516898

[Non-Patent Document 1] Carl Hess et al. (KLA-Tencor Corporation), A Novel Approach: High Resolution Inspection with a Wafer Plane Defect Detection. Prof of SPIE Vol. 7028, 70281F (2008)

[Non-Patent Document 2] Dan Ros et al. (MP-Mask Technology Center) Qualification of Aerial Image 193 nm Inspection Tool for All Masks and All Process Steps, Proc of SPIE Vol. 7028, 70282Q (2008).

In a process of determining defects, an operator checks the result indicated by a defect inspection apparatus. This process is referred to as "review process". In the review process, for example, a device having an optical system prepared to detect a defect and a reviewing optical system is used. Further, a stage is moved to a coordinate of the defect detected in the defect inspection, and the defect portion is displayed as if seen through a microscope by means of the reviewing optical system. In this case, a sampled image of the inspection apparatus based on which the defect is identified is also aligned and displayed. By this means, the operator determines whether or not the defect detected by the defect inspection apparatus is a true defect and whether or not the defect needs to be repaired, and makes a classification.

The review screen consists of, a window, through which the reference image as the basis for the defect determination and the optical image including the defect are displayed so that the operator can compare the reference image and the optical image, and a window through which the defect distribution in the inspection range on the mask is displayed. There may be further provided a profile screen window through which a difference between the optical image and the reference image is displayed, the brightness of each pixel of the optical image and the reference image are dump displayed with numeric values, and the sensor brightness is displayed when sectioned by the x and y axes for the purpose of analyzing the defect.

Following the miniaturization of a mask pattern in recent years, the wavelength of light from a light source used for inspecting a defect can be made shorter thereby becoming ultraviolet light. When this pattern is reviewed, the pattern cannot be visually checked with visible light, and images need to be acquired with a camera using ultraviolet light. Hence, the inspection apparatus on which the reviewing optical system is not mounted is usually used to display and review an optical image including a defect, which is recorded when the defect is determined and based on which the defect is identified, and a reference image of the optical image. In this case, the inspection apparatus does not have to perform reviewing, and it is possible to browse a test result recorded in the inspection apparatus using a personal computer additionally prepared.

The review process can also be performed based on a transfer estimation image to a wafer generated from an image including the defect of a mask sampled by the inspection apparatus. That is, it is possible to indicate an optical image using the reviewing optical system, and display and review the transfer estimation image. In this case, it may be possible to review the transfer estimation image using a reviewing operation terminal prepared in addition to the inspection apparatus.

When one defect on the mask detected by the inspection apparatus leads to discovery of a plurality of defects in a transfer estimation image, it is necessary to visually check the latter defects one by one and learn the degree of influence the defect on the mask has on the transfer estimation image, and identify the defects on the mask. For example, even when the degree of defect dimensions on the mask is the same, the criticality in the transfer estimation image differs depending on the pattern site at which the defect is produced. For example, a pattern which has a narrow line width used to transmit a clock signal of LSI needing to be uniformly formed, and a pattern which has a comparatively wide line width used for a power source are taken into account. Even when the former pattern includes a defect which causes critical fluctuation in the line width, if the degree of this fluctuation is the same even for the latter pattern, the influence on the latter defect may be negligible.

The present invention has been conceived in view of the above problem. Therefore, an object of this invention is to provide an inspection apparatus and an inspection method, which can estimate a defect on a mask and the resulting influence on a wafer, and perform defect determination efficiently.

Other challenges and advantages of the present invention are apparent from the following description.

SUMMARY OF THE INVENTION

The present invention relates to an Inspection apparatus and Method, in a first embodiment of this invention:

An inspection apparatus which determines whether or not there is a defect by irradiating light on to a sample on which a pattern is formed and forming an image of the sample on an image sensor by means of an optical system, the inspection apparatus comprising: an optical image acquiring unit which acquires an optical image of the sample from the image sensor, a first comparing unit which compares the optical image with a reference image which serves as a reference of the determination, and identifies a defect when a difference exceeds a first threshold, a transfer image estimating unit which estimates a transfer image when patterns of the optical image on the sample and the reference image are transferred by a transfer device, a second comparing unit which compares each of the transfer images and identifies a defect when a difference exceeds a second threshold, and a review device which reviews information from the first comparing unit and the second comparing unit.

In another aspect of this apparatus, an inspection apparatus, wherein the review device preferentially reviews a greater value of an error ratio calculated for a line width of the pattern and an error ratio calculated for an inter-line distance between the patterns.

In another aspect of this apparatus, an inspection apparatus, wherein the review device performs review in order of following (1) to (3):
(1) when the degree of a defect identified in the first comparing unit is a third threshold or above and an error ratio of a line width or an inter-line distance of a defect corresponding to the defect and identified in the second comparing unit is a fourth threshold or above,
(2) when the degree of a defect identified in the first comparing unit is less than the third threshold, and an error ratio of a line width or an inter-line distance of a defect corresponding to the defect and identified in the second comparing unit is the fourth threshold or above, and
(3) when the degree of a defect identified in the first comparing unit is the third threshold or above, and an error ratio of a line width or an inter-line distance of a defect corresponding to the defect and identified in the second comparing unit is less than the fourth threshold.

In another aspect of this apparatus, an inspection apparatus, wherein the review device reviews a defect within a predetermined dimension from a position of the transfer image corresponding to a position at which a defect is identified in the first comparing unit with the defect identified in the second comparing unit.

In another aspect of this apparatus, an inspection apparatus, wherein the review device preferentially reviews a greater value of a pattern density in one direction of the patterns, and a pattern density in a direction vertical to the one direction.

In a second embodiment of this invention, an inspection apparatus which determines whether or not there is a defect by irradiating light on to a sample on which a pattern is formed and forming an image of the sample on an image sensor by means of an optical system, the inspection apparatus comprising: an optical image acquiring unit which acquires optical images of a sample from the image sensor, a first comparing unit which compares a first optical image with a second optical image, and identifies a defect when a difference exceeds a first threshold, a transfer image estimating unit which estimates a transfer image when patterns of the first optical image on the sample and the second optical image are transferred by a transfer device, a second comparing unit which compares each of the transfer images and identifies a defect when a difference exceeds a second threshold, and a review device which reviews information from the first comparing unit and the second comparing unit.

In another aspect of the second embodiment, an inspection apparatus, wherein the review device preferentially reviews a greater value of an error ratio calculated for a line width of the pattern and an error ratio calculated for an inter-line distance between the patterns.

In another aspect of the second embodiment, an inspection apparatus, wherein the review device performs review in order of following (1) to (3):
(1) when the degree of a defect identified in the first comparing unit is a third threshold or above and an error ratio of a line width or an inter-line distance of a defect corresponding to the defect and identified in the second comparing unit is a fourth threshold or above,
(2) when the degree of a defect identified in the first comparing unit is less than the third threshold, and an error ratio of a line width or an inter-line distance of a defect corresponding to the defect and identified in the second comparing unit is the fourth threshold or above, and
(3) when the degree of a defect identified in the first comparing unit is the third threshold or above, and an error ratio of a line width or an inter-line distance of a defect corresponding to the defect and identified in the second comparing unit is less than the fourth threshold.

In another aspect of the second embodiment, an inspection apparatus, wherein the review device reviews a defect within a predetermined dimension from a position of the transfer image corresponding to a position at which a defect is identified in the first comparing unit with the defect identified in the second comparing unit.

In another aspect of the second embodiment, an inspection apparatus, wherein the review device preferentially reviews a greater value of a pattern density in one direction of the patterns and a pattern density in a direction vertical to the one direction.

In a third embodiment of this invention, an inspecting method of determining whether or not there is a defect by irradiating light on to a sample on which a pattern is formed and forming an image of the sample on an image sensor by means of an optical system, the inspecting method comprising: acquiring an optical image of the sample from the image sensor, comparing the optical image with a reference image which serves as a reference of the determination, and identifying a defect when a difference exceeds a first threshold, estimating a transfer image of the optical image and a transfer image of the reference image, comparing the transfer image of the optical image with the transfer image of the reference image and identifying a defect when a difference exceeds a second threshold, and reviewing each of the transfer images in order of following (1) to (3):
(1) when the degree of a defect identified in the first comparing unit is a third threshold or above and an error ratio of a line width or an inter-line distance of a defect corresponding to the defect and identified in the second comparing unit is a fourth threshold or above,
(2) when the degree of a defect identified in the first comparing unit is less than the third threshold, and an error ratio of a line width or an inter-line distance of a defect corresponding to the defect and identified in the second comparing unit is the fourth threshold or above, and
(3) when the degree of a defect identified in the first comparing unit is the third threshold or above, and an error ratio of a line width or an inter-line distance of a defect corresponding to the defect and identified in the second comparing unit is less than the fourth threshold.

In a forth embodiment of this invention, an inspecting method of determining whether or not there is a defect by irradiating light on to a sample on which a pattern is formed and forming an image of the sample on an image sensor by means of an optical system, the inspecting method comprising: acquiring optical images of a sample from the image sensor, comparing a first optical image with a second optical image and identifying a defect when a difference exceeds a first threshold, estimating a transfer image of the first optical image and a transfer image of the second optical, comparing the transfer image of the first optical image with the transfer image of the second optical image and identifying a defect when a difference exceeds a second threshold, and reviewing each of the transfer images in order of following (1) to (3):

(1) when the degree of a defect identified in the first comparing unit is a third threshold or above and an error ratio of a line width or an inter-line distance of a defect corresponding to the defect and identified in the second comparing unit is a fourth threshold or above, (2) when the degree of a defect identified in the first comparing unit is less than the third threshold, and an error ratio of a line width or an inter-line distance of a defect corresponding to the defect and identified in the second comparing unit is the fourth threshold or above, and (3) when the degree of a defect identified in the first comparing unit is the third threshold or above, and an error ratio of a line width or an inter-line distance of a defect corresponding to the defect and identified in the second comparing unit is less than the fourth threshold.

BRIEF DESCRIPTION OF THE DRAWINGS

FIG. 4 is a diagram illustrating the way in which acquired mask data is acquired according to the present embodiment.

FIG. 6a is a reference image of a mask created from the design data according to the present embodiment.

FIG. 6b is a wafer transfer image estimated from the reference image according to the present embodiment.

FIG. 10a is a wafer transfer image of a mask having a defect in the shape.

FIG. 10b is a diagram illustrating the horizontal width or vertical width of the above wafer transfer image.

FIG. 12 is an example of a hole pattern arranged in a matrix pattern, in which each interval in the vertical direction and horizontal direction is different.

FIG. 13 illustrates the priority into which a defect is classified by taking into account the criticality of the defect.

DETAILED DESCRIPTION OF THE EMBODIMENTS

Figure 1:
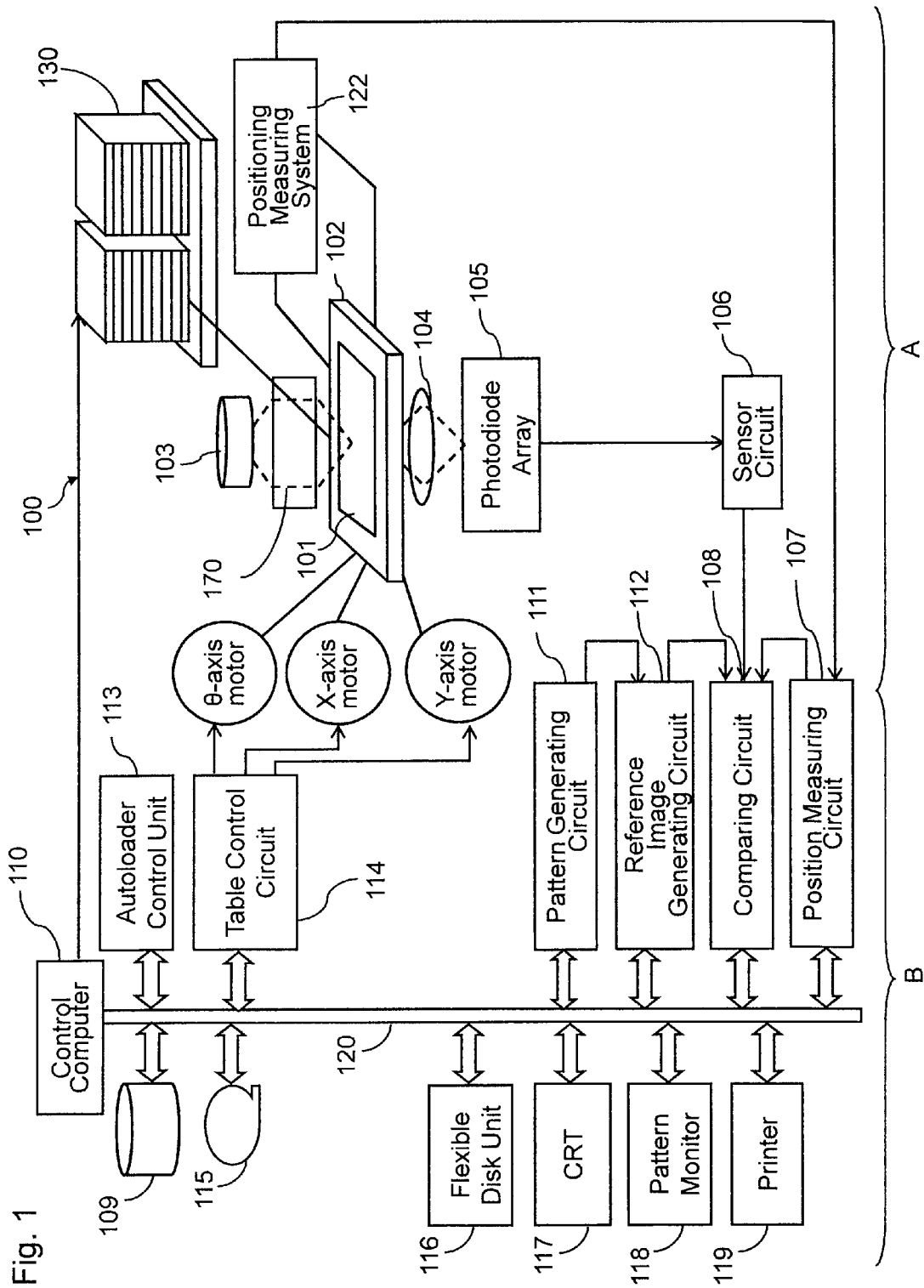
FIG. 1 is a diagram showing the configuration of an inspection apparatus according to Embodiment 1.

FIG. 1 is a diagram showing the configuration of an inspection apparatus according to an Embodiment of the present invention. The inspection apparatus of the present Embodiment will be described in connection with the inspection of masks used in photolithography.

As shown in FIG. 1, the inspection apparatus 100 includes an optical image acquiring unit A and a control unit B.

The optical image acquiring unit A includes a light source 103, an XYθ table 102 movable in the horizontal X and Y directions and rotatable in a horizontal plane (or in a θ direction), an optical illumination system 170 serving as a transmission illumination system, an enlarging optical system 104, a photodiode array 105, a sensor circuit 106, a position measuring system 122, and an autoloader 130.

In the control unit B, a control computer 110 which controls the entire inspection apparatus 100 is connected through a bus 120 (serving as a data transmission path) to a position measuring circuit 107, a comparing circuit 108, a reference circuit 112, a pattern generating circuit 111, an autoloader control unit 113, a table control circuit 114, a storage unit 109 serving as storage units, a magnetic tape unit 115, a flexible disk unit 116, a CRT 117, a pattern monitor 118, and a printer 119. The XYθ table 102 is driven by X-, Y-, and θ-axis motors controlled by the table control circuit 114. These motors may be, for e.g., step motors.

Design pattern data used as reference data in database inspection is stored in the storage unit 109. This data is read out and sent to the pattern generating circuit 111 when necessary in the course of the inspection process. The pattern generating circuit 111 converts the design pattern data into image data (or bit pattern data). This image data is then sent to the reference circuit 112 for generation of reference data.

It should be noted that the inspection apparatus of the present Embodiment may include, in addition to the components shown in FIG. 1 described above, other known components required to inspect masks.

Figure 2:
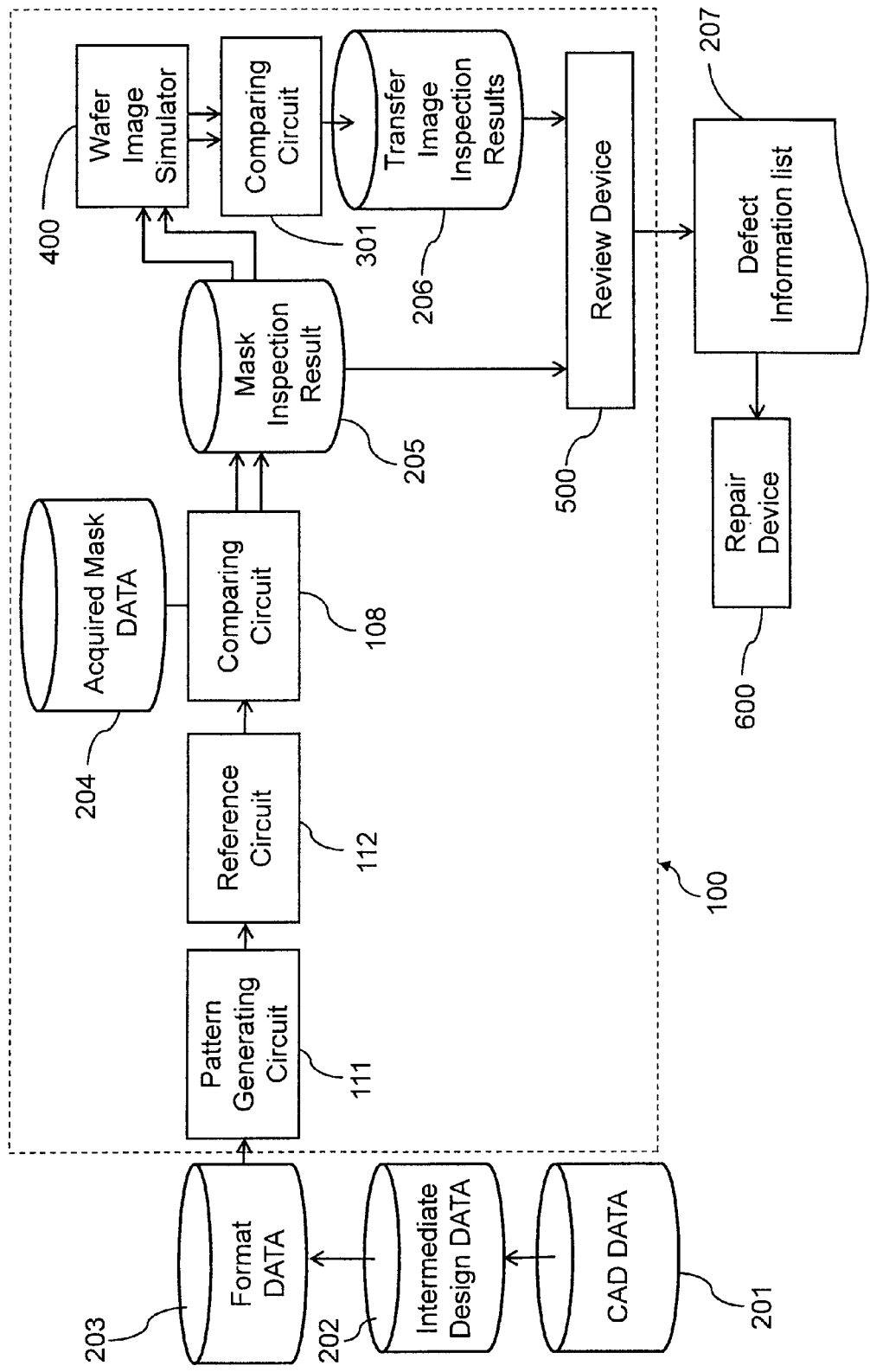
FIG. 2 is a schematic diagram showing a flow of data according to the present embodiment.

FIG. 2 is a schematic diagram showing a flow of data according to the present Embodiment.

As shown in FIG. 2, CAD data 201 prepared by the designer (or user) is converted to intermediate design data 202 in a hierarchical format such as OASIS. The intermediate design data 202 includes data of the pattern formed on the mask created for each layer. It should be noted that, generally, writing apparatuses are not adapted to be able to directly read OASIS data. That is, each manufacturer of writing apparatus uses different format data. Therefore, OASIS data is converted, for each layer, to format data 203 in a format specific to the inspection apparatus 100 used, and this format data 203 is input to the inspection apparatus 100 of FIG. 1. Although the format data 203 may be data specific to the inspection apparatus 100, the format data 203 may also be data compatible with a drawing device.

The format data 203 is input to the storage unit 109 of FIG. 1. The design pattern data that was used to form the pattern on the photomask 101 is stored in the storage unit 109.

The designed pattern includes pattern features each consisting of basic features such as rectangles and triangles. The storage unit 109 stores feature data indicating the shape, size, and position of each pattern feature, specifically, e.g., information such as the coordinates (x, y) of the reference position of each feature, the length of its sides, and a shape code (or identifier) identifying the type of shape such as a rectangle or triangle.

Further, a group of pattern features, defined in an area of approximately a few tens of micrometers square is referred to as a "cluster" or "cell". It is common practice that the design pattern data is defined in a hierarchical structure using clusters or cells. A cluster (or cell), which contains a pattern feature or features, may be used alone or repeated at certain intervals. In the former case the coordinate positions of the cluster (or cell) on the photomask are specified, whereas in the latter case the coordinate positions of each copy of the cluster (or cell) are indicated together with a repetition instruction. Each cluster (or cell) is disposed in a strip-shaped region, referred to as a "frame" or "stripe", having a width of a few hundreds of micrometers and a length of approximately 100 mm which corresponds to the length of the photomask in the X or Y direction.

The pattern generating circuit 111 reads design pattern data of the photomask 101 from the storage unit 109 through the control computer 110.

Specifically, upon reading the design pattern data, the pattern generating circuit 111 generates data of each pattern feature, and interprets the shape code in the data indicative of the shape of the pattern feature and obtains its dimensions. The pattern generating circuit 111 then divides the pattern into an imaginary grid of squares (or grid elements) having predetermined quantization dimensions, and produces 2-bit or other multiple-bit design image data of the design pattern segment in each grid element. By using the produced design image data, the pattern generating circuit 111 calculates the design pattern occupancy in each grid element (corresponding to a sensor pixel). This pattern occupancy in each pixel represents the pixel value.

The design pattern data is converted into 2-bit or other multiple-bit image data (design image data). This image data is sent to the reference circuit 112. After receiving the design image data (i.e., image data of the pattern), the reference circuit 112 performs appropriate filtering on the data.

Figure 3:
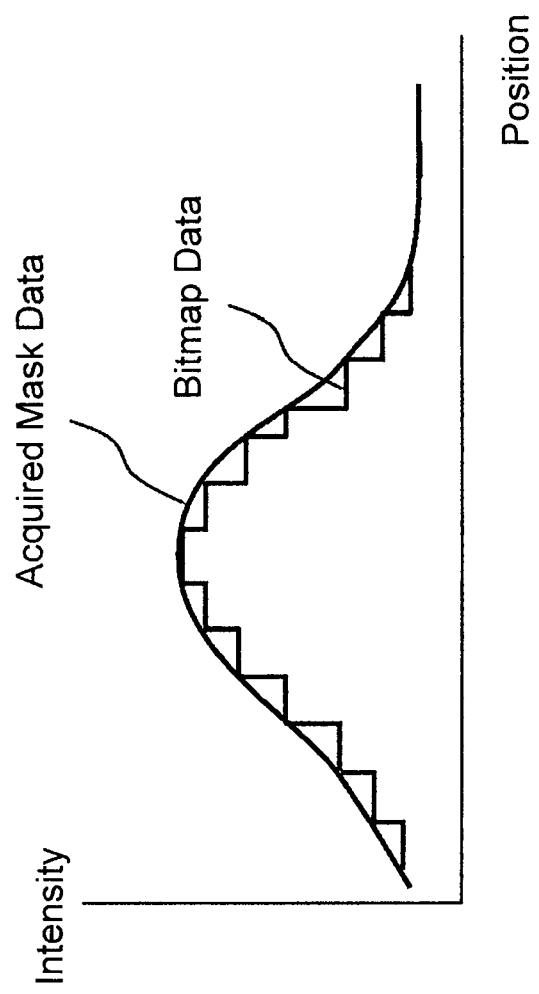
FIG. 3 is a diagram illustrating the filtering according to the present embodiment.

FIG. 3 is a diagram illustrating the filtering.

The optical image, i.e. the acquired mask data 204, output from the sensor circuit 106 is somewhat "blurred" due to the resolution characteristics of the enlarging optical system 104 and due to the aperture effect in the photodiode array 105, that is, this optical image is a spatially low-pass filtered image. Therefore, since the design image data corresponding to the optical image is digital data consisting of digital values representing the intensity (or gray scale) of each point of the image, this design image data may be filtered to match the "blurred" optical image, or measurement data. In this way, a reference image to be compared with the optical image is produced.

Next, a method of obtaining the acquired mask data 204 will be described using FIGS. 1 and 4.

The optical image acquiring unit A shown in FIG. 1 acquires an optical image (i.e. acquired mask data 204) of a photomask 101. It will be noted that this acquired mask data 204 includes an image of a pattern on the mask, this pattern was written in accordance with the corresponding design pattern data. The detailed method of acquiring this mask data 204 is as follows.

The photomask 101 serving as an inspection workpiece is mounted on the XYθ table 102 provided to be movable in two horizontal directions by X- and Y-axis motors and rotatable in a horizontal plane by a θ-axis motor. The pattern formed on the photomask 101 is then irradiated with light emitted from the light source 103 disposed above the XYθ table 102. More specifically, the beam of light emitted from the light source 103 passes through the optical illumination system 170 and is irradiated to the photomask 101. The enlarging optical system 104, the photodiode array 105, and the sensor circuit 106 are disposed below the photomask 101. The light transmitted through the photomask 101 passes through the enlarging optical system 104 and reaches the photodiode array 105, thereby forming an optical image thereon. It should be noted that the enlarging optical system 104 may have its focus automatically adjusted by an autofocus mechanism (not shown). Further, though not shown, the inspection apparatus 100 may be constructed so that light is also emitted from a source below the photomask 101, and the reflected light is passed through an enlarging optical system to a second photodiode array, thus acquiring the transmitted light and the reflected light simultaneously.

FIG. 4 is a diagram illustrating the way in which mask data 204 is acquired.

The inspection area is divided into a plurality of strip-shaped inspection stripes 20 by imaginary lines running in the X direction, where the width of each inspection stripe 20 in the Y direction is equal to the scan width W, as shown in FIG. 4. The movement of the XYθ table 102 is controlled so that each inspection stripe 20 is continuously scanned in the negative or positive X direction with the light to acquire an image of the inspection stripe. At that time, the photodiode array 105 continuously generates an image (of each inspection stripe 20) having a width corresponding to the scan width W, as shown in FIG. 4. After acquiring an image of a first inspection stripe by scanning it, e.g., in the negative X direction, a second inspection stripe is continuously scanned in the positive (i.e., opposite) X direction to acquire an image of a width corresponding to the scan width W. Likewise, a third inspection stripe is scanned in the negative x direction (opposite the direction in which the second inspection stripe is scanned, and in the same direction as the first inspection stripe) to acquire an image. This way of continuously acquiring an image of one inspection stripe 20 after another reduces waste of processing time.

The pattern image formed on the photodiode array 105 as shown in FIG. 1 is photoelectrically converted by the photodiode array 105 and A/D (analog to digital) converted by the sensor circuit 106. The photodiode array 105 is made up of sensors arranged in an array. These sensors may be, e.g., TDI (Time Delay Integration) sensors. Thus, the pattern on the photomask 101 is imaged by these TDI sensors while the XYθ table 102 is continuously moved in the positive or negative X direction. It should be noted that the light source 103, the enlarging optical system 104, the photodiode array 105, and the sensor circuit 106 together form a high power optical inspection apparatus.

The XYθ table 102 can be moved in the X and Y directions and rotated in a θ direction (or in an XY plane) by a drive system such as a 3-axis (X-Y-θ) motor driven by the table control circuit 114 under the control of the control computer 110. These X-, Y-, and θ-axis motors may be, e.g., step motors. The position of the XYθ table 102 is measured by the position measuring system 122, and the measurement data is sent to the position measuring circuit 107. Further, the photomask 101 is automatically loaded onto the XYθ table 102 from the autoloader 130 driven by the autoloader control unit 113, and, upon completion of its inspection, the photomask 101 is automatically retrieved from the XYθ table 102.

Acquired mask data 204 output from the sensor circuit 106 is sent to the comparing circuit 108, i.e. first comparing unit, together with data indicative of the position of the photomask 101 on the XYθ table 102, this data is output from the position measuring circuit 107. The measurement data is, for example, unsigned 8-bit data representing the gray scale of each pixel. The reference image is then sent to the comparing circuit 108.

The comparing circuit 108 compares each portion of the acquired mask data 204 received from the sensor circuit 106 with the corresponding portion of the reference image generated by the reference circuit 112 in accordance with a suitable comparison determination algorithm, and if the difference, for example, in dimension, between these portions exceeds a predetermined value (the first threshold), the comparing circuit 108 determines that the portion of the optical image is defective. The optical image to be compared may be a transmission image or a reflection image or a combination thereof, and the algorithm is selected to be suitable for the image to be compared. If it is determined from the comparison that a portion of the optical image is defective, then the coordinates of that portion, the acquired mask data 204, and the reference image, on which the detection of the defect is based, are stored as a mask inspection result 205 in storage unit 109.

Incidentally, defects associated with micropatterns include not only shape defects typified by pattern edge roughness, but also pattern linewidth errors and pattern displacement errors, which are becoming more and more significant due to the miniaturization of a device pattern on a mask. Therefore, there has been a strong need to accurately control the dimensions of patterns, thus increasing the difficulty of manufacturing masks. As a result, there has been loss in the yield of masks that meet required specifications, thereby raising mask manufacturing cost. In order to address this problem, a defect evaluating method has been proposed which uses a wafer image simulator (lithography simulator or process simulator). This method simulates the image which would be printed from the mask to a wafer by the photolithography apparatus and determines whether or not the pattern on the mask is defective by inspecting the simulated image. The wafer image simulator 400 is a transfer image estimating unit of the present invention.

The mask inspection result 205 stored in the storage unit 109 is sent to the wafer image simulator 400. Instead of the reference image of mask inspection result 205, an image obtained by simulating a mask production process from pattern data prior to addition of a RET pattern of mask design may be used.

In the wafer image simulator 400, the wafer transfer image is estimated by simulation. Specifically, the wafer transfer image is estimated from the reference image as a model, and, at the same time, the wafer transfer image is also estimated from the mask data 204. Thereafter, the wafer transfer images are sent from the wafer image simulator 400 to a comparing circuit 301 (a second comparing unit).

In the comparing circuit 301, the wafer transfer image estimated from the reference image and the wafer transfer image estimated from the mask data 204 are compared with each other using an appropriate comparative determination algorithm. When it is determined that there is a defect, the coordinate and the wafer transfer image as a basis for the defect determination are stored as transfer image inspection results 206.

The mask inspection results 205 and the transfer image inspection results 206 are sent to the review device 500. The operator determines whether a pattern defect found in the inspection can be tolerated. However, when the defect detected in the wafer transfer image is minor, the defect may be excluded from an object to be reviewed by pre-processing.

In this review process, the operator determines whether a pattern defect found in the inspection can be tolerated. The operator compares the reference image, as the basis for the defect determination, with the optical image including the defect and reviews. If the pattern shape formed in the mask is relatively simple, the operator can predict the position of defects on the wafer from position the of the mask defect without starting the wafer image simulator 400.

Meanwhile, when a minute pattern is formed in the mask, it is difficult to judge the necessity of modification. Transfer image inspection results 206 are sent to the review device 500 for review, the review is performed by the operator and thus the operator can compare the reference image, the optical image, and transfer image estimated from these for review.

To observe defect coordinates of defects one by one, the review device 500 displays images of defect portions on a mask using the observing optical system of the inspection apparatus 100 while moving the table on which the mask is set. Simultaneously, the review device 500 aligns and displays optical images and reference images which serve as an identification condition or identification ground, on the screen to check. For this screen, the screen of the control computer 110 or the screen of a calculator which is additionally prepared is utilized. By aligning and displaying the defects on the mask and the condition of influence on a wafer transfer image in the review process, it becomes easy to determine whether or not the mask pattern needs to be repaired. In addition, generally, projection from the mask to the wafer is performed while reduction to approximately quarter size is performed, and therefore this reduction scale is taken into account when the defects and the condition of influence are aligned and displayed.

Figure 7:
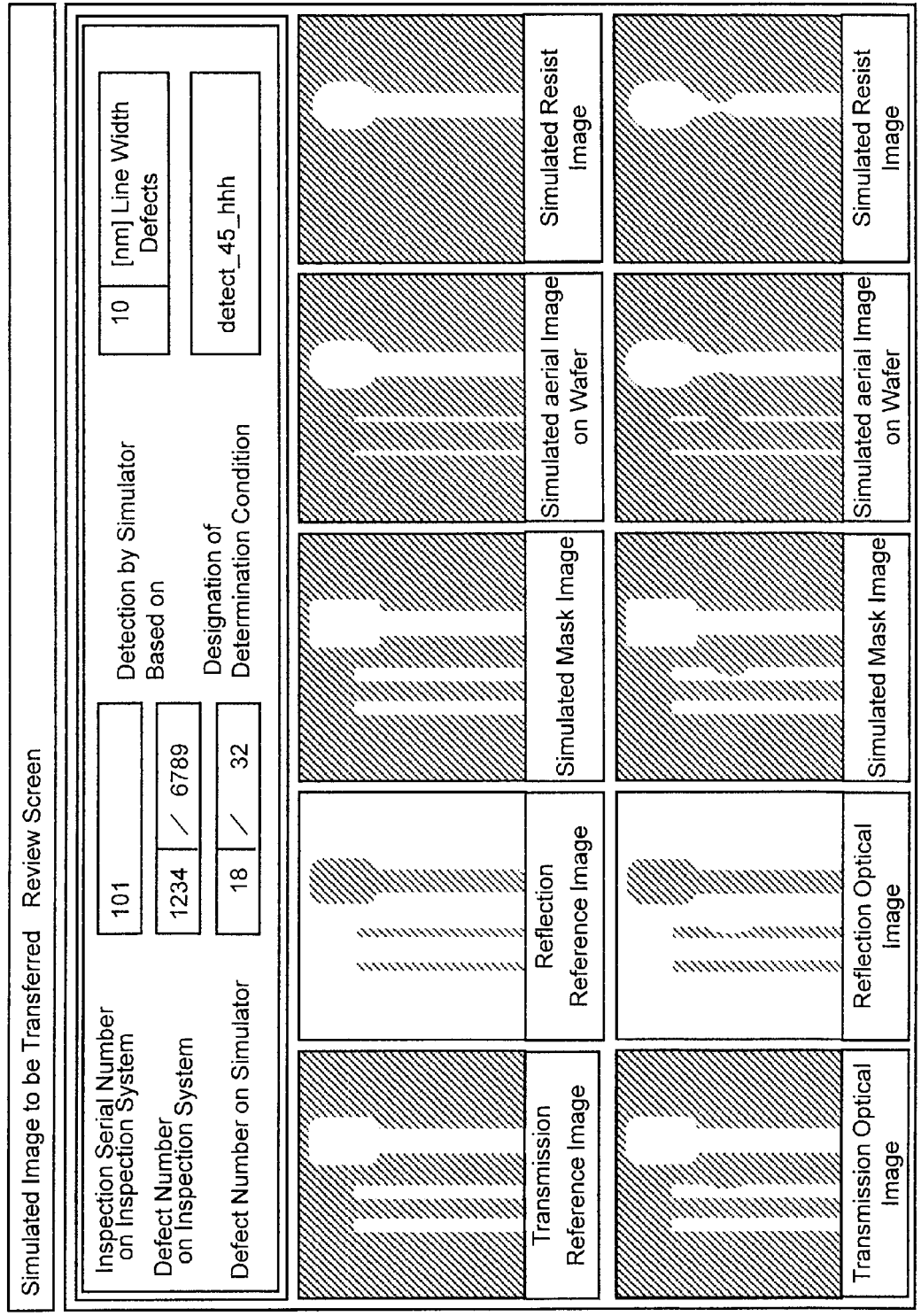
FIG. 7 is a review screen through which an operator browses the results of the defect determination based on the wafer transfer image and the resist image according to the present embodiment.

FIG. 7 is a screen through which an operator browses the results of the defect determination based on the wafer transfer image and the resist image. The upper stage, displayed on the top half of the screen, is a reference image or an optical image using a die-to-die comparing method. The lower stage, displayed on the bottom half of the screen, is an optical image including the defect. In each stage, the images are (1) an image taken by a transmission optical system of the inspection apparatus, (2) an image taken by a reflection optical system of the inspection apparatus, (3) a mask image estimated from these images, (4) a wafer transfer image obtained by simulating and estimating exposure conditions based on the mask image, and (5) a resist image obtained by simulating and estimating characteristics of resist in sequence from the left of FIG. 7.

The review screen illustrated in FIG. 7 aligns and displays the reference image, optical image, and transfer image estimated from these images, so that the operator can compare these images, and analyze the defects on the mask in detail and narrow down defects which need to be repaired.

Figure 8:
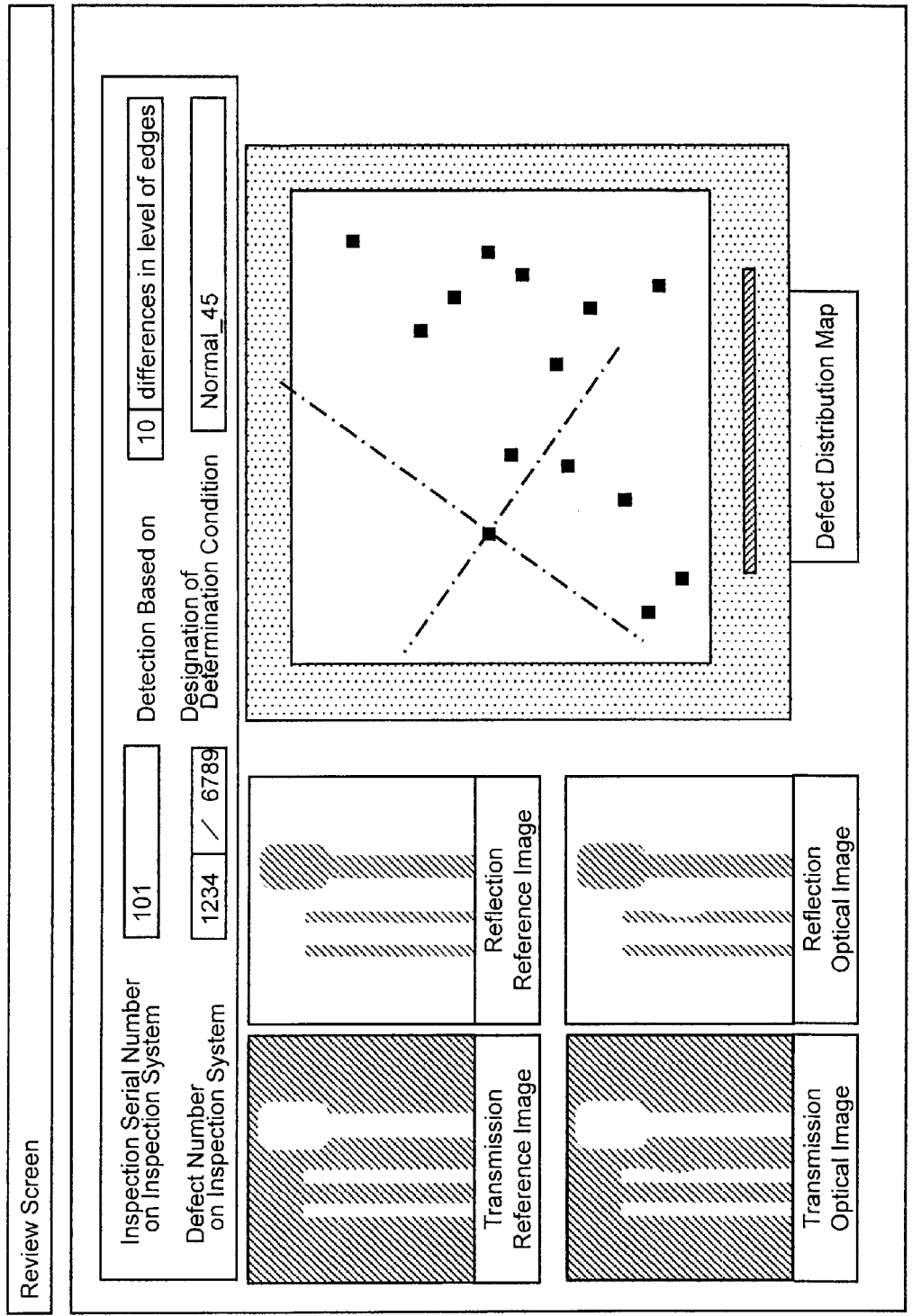
FIG. 8 shows another example of the review screen for reviewing a mask defect in the inspection apparatus according to the present embodiment.

FIG. 8 shows an example of the review screen for reviewing a mask defect in the inspection apparatus. The screen consists of, a window, through which the reference image as the basis for the defect determination, and the optical image including the defect are displayed so that the operator can compare the reference image and the optical image, and a window through which the defect distribution in the inspection range on the mask is displayed. There may be further provided a profile screen window through which a difference between the optical image and the reference image is displayed, the brightness of each pixel of the optical image and the reference image are dump displayed with numeric values, and the sensor brightness is displayed when sectioned by the x and y axes for the purpose of analyzing the defect.

As described above, in the review process,
(1) An optical image of transmitted light sampled in the inspection apparatus;
(2) An optical image of reflected light sampled in the inspection apparatus;
(3) A virtual mask image estimated from the image of the transmitted light and the image of the reflected light;
(4) A light intensity distribution image on a projection plane reduced and projected on a wafer simulating an exposure device; and
(5) A resist image estimated by taking into account resist characteristics, are displayed on the review screen. Further, when a transfer estimation image generated from the optical image and a transfer estimation image generated from the reference image are compared in the resist image of (5) and there is a difference in the line width or inter-line distance between patterns, the operator identifies this portion as a defect. In this case, the identification by the operator may be helped by, for example, superimposing an outline of the pattern on the image.

In the present embodiment, in the review process, it is also possible to use the light intensity distribution image of (4) on the wafer projection plane instead of the above resist image of (5), and identify defects in the transfer estimation image. In this case, the outline of the light intensity distribution image and the outline of the resist image in the wafer projection plane are equivalent. That is, an offset value and amplitude are adjusted such that the outline of the light intensity distribution image is drawn with an appropriate threshold.

As described above, when it is determined that there is a defect, the acquired mask data used as a basis for the determination and the corresponding reference image are stored in the inspection apparatus along with their coordinates. When the inspection of one mask is completed, an operator visually confirms a pattern at a defect portion utilizing an observation optical system in the inspection apparatus. Then, the necessity of repair is determined. After a defect to be repaired is determined, the mask and the information required for the repair are sent to a repair device. The information required for the repair is cut-out pattern data for use in the recognition of, coordinates in the mask, discrimination between extrusion and intrusion defects, discrimination whether to remove a light-shielding film or deposit a pattern at a portion to be repaired by the repair device. The above acquired mask data can be utilized as the cut-out pattern data.

As shown in FIG. 1 and FIG. 2, the information of a defect determined through the review process is saved in the storage unit 109. When even one defect to be repaired is confirmed in the review device 500, the mask is sent to a repair device 600, which is an external device of the inspection apparatus 100, with a defect information list 207.

Since the repair method is different according to the type of defect, that is, between the extrusion and intrusion defects, the type of the defect including determination between the extrusion and intrusion defects and the coordinates of the defect are added to the defect information list 207.

Identification of defects using a light intensity distribution image or a resist image on the wafer projection plane can be performed according to the next two types of methods. One method is directed to identifying defects when there is a difference exceeding a predetermined threshold dimension between a position of the outline of the transfer estimation image generated from the reference image and a position of the outline of the transfer estimation image generated from the optical image. The other one is directed to identifying defects when the ratio of the line width of the pattern in the transfer estimation image generated from the reference image and the line width of the pattern in the transfer estimation image generated from the optical image exceeds a predetermined threshold. With the latter method, the ratio of the distance between patterns in the transfer estimation image generated from the reference image and the distance between patterns in the transfer estimation image generated from the optical image may be used for identification of defects. In addition, the above thresholds each correspond to a second threshold according to the present invention.

Figure 5B:
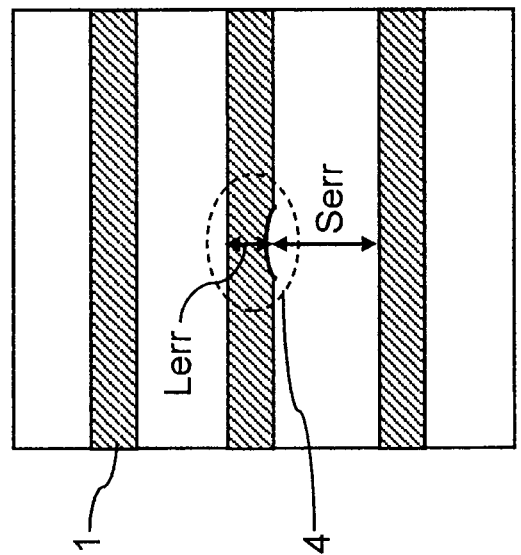
FIG. 5b is a wafer transfer image obtained by simulation of the above according to the present embodiment.
Figure 5A:
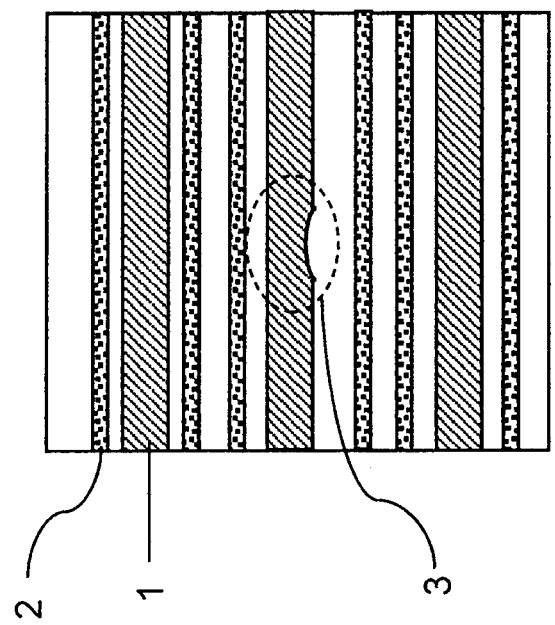
FIG. 5a is an example of the defect on a mask according to the present embodiment.

FIG. 5a is an example of a defect on a mask. In this example, there is a defect in the main pattern 1 as shown in region 3. The assist pattern 2 is a pattern, which is auxiliary provided on a mask for the purpose of improving the patterning characteristics of a main pattern 1, the assist pattern 2 is not transferred onto a wafer. When a wafer transfer image on the mask in FIG. 5a is estimated by simulation, the wafer transfer image shown in FIG. 5b is obtained. That is, in the wafer transfer image, the line width at the defect portion is smaller than the line width of a pattern at a normal portion. When the degree of reduction in the line width is more than a specified value, the defect portion, as shown in region 4, is determined as the defect portion to be repaired, this determination is then recorded. The degree of reduction in the line width may be specified by a difference of an estimated line width between the normal portion and the defect portion, or may be specified by the ratio of the estimated line width of the defect portion to the normal portion.

FIG. 6a shows an example of a reference image created from the design data, this reference image is a reference image of the optical image as shown in FIG. 5a. In addition, FIG. 6b is the estimated image transfer from the reference image of FIG. 6a. Determination as to whether the defect detected in region 3, as shown in FIG. 5a, should be repaired or not is performed by comparing transferred estimate images of FIG. 5a and FIG. 5b.

The determination of defect in region 3 is performed by calculating a measured error or error ratios of line width, or the distance between the inter-line distance.

A measured error of the line width is found according to formula (1). Further, the measured error of the inter-line distance is found according to formula (2). Meanwhile, the line width of the defect portion in the transfer estimation image is Lerr, and the inter-line distance is Serr. Further, in the transfer estimation image generated from the reference image, the line width which serves as a comparison basis is Lref, and the inter-line distance is Sref.

$$ErrCD = |Lerr - Lref| \tag{1}$$

$$ErrCD = |Serr - Sref| \tag{2}$$

The error ratio of the line width is found according to formula (3). Further, the error ratio of the inter-line distance is found according to formula (4). Meanwhile, the line width at the defect portion in the transfer estimation image is Lerr, and the inter-line distance is Serr. Further, in the transfer estimation image generated from the reference image, the line width which serves as a comparison basis is Lref, and the inter-line distance is Sref.

$$ErrCD = \left|\frac{Lerr - Lref}{Lref}\right| \times 100 \tag{3}$$

$$ErrCD = \left|\frac{Serr - Sref}{Sref}\right| \times 100 \tag{4}$$

When, for example, reduction projection at quarter size is performed from a mask to a wafer, the pattern having the line width of 200 nm and the inter-line distance of 180 nm on the mask has a line width of 50 nm and an inter-line distance of 45 nm on the wafer. When there is a defect that the line width becomes 5 mm wider in the wafer transfer image, the error ratio of the line width is found according to the following formula.

$$ErrCD = \frac{Lerr - Lref}{Lref} \times 100[\%]$$
$$= \frac{5}{50} \times 100$$
$$= 10[\%]$$

In addition, error ratio of the inter-line distance in the above-mentioned example, is calculated by the following formula.

$$ErrCD = \frac{Serr - Sref}{Sref} \times 100[\%]$$

$$= \frac{-5}{45} \times 100$$

$$= -11.1[\%]$$

When error ratio of line width and error ratio of inter-line distance are compared, error ratio of line width is larger. Thus, in the review process it is preferred to show the error of line width ratio.

In the present embodiment, of the error ratio calculated for the line width of the pattern and the error ratio calculated for the inter-line distance of the pattern, the greater value is preferably reviewed preferentially. Further, it is difficult to find an edge pair depending on the size of a pattern, and therefore it is preferable to make identification using the error ratio and measured error in combination.

Figure 9B:
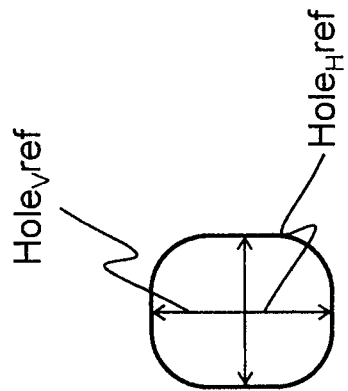
FIG. 9b is a diagram illustrating the horizontal width or vertical width which serves as a comparison basis in the above wafer transfer image.
Figure 9A:
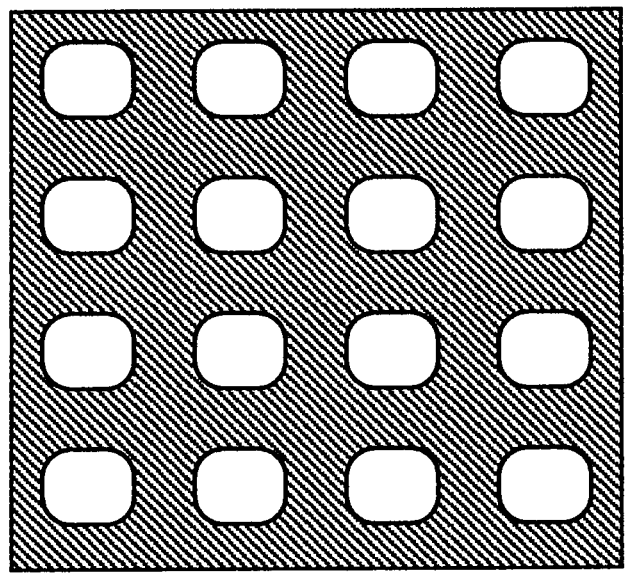
FIG. 9a is a wafer transfer image estimated from the reference image according to the present embodiment.

FIG. 9a illustrates a transfer estimation image created using the reference image estimated from design data. In this example, the pattern to be formed is a hole pattern instead of a stripe pattern. By contrast with this, FIG. 10a illustrates an estimation image to be transferred to the wafer using a mask having a defect in the shape. In this example, the area 5 has a defect that a hole diameter is smaller than the transfer estimation image estimated from the reference image.

Identification of the defect in the area 5 is performed by calculating the measured error or error ratio of the horizontal width or vertical width of the hole diameter.

The measured error of the horizontal width is found according to formula (5). Further, the measured error of the vertical width is found according to formula (6). Meanwhile, as illustrated in FIG. 9b, in the transfer estimation image generated from the reference image, the horizontal width which serves as a comparison basis is HoleHref, and the vertical width is HoleVref. Further, as illustrated in FIG. 10b, in the transfer estimation image in which there is a defect portion, the horizontal width is HoleHerr, and the vertical width is HoleVerr.

$$ErrCD = (Hole_H err - Hole_H ref) \quad (5)$$

$$ErrCD = (Hole_V err - Hole_V ref) \quad (6)$$

The error ratio of the horizontal width is found according to formula (7). Further, the error ratio of the vertical width is found according to formula (8). Meanwhile, as illustrated in FIG. 9b, in the transfer estimation image generated from the reference image, the horizontal width which serves as a comparison basis is HoleHref, and the vertical width is HoleVref. Further, as illustrated in FIG. 10b, in the transfer estimation image in which there is a defect portion, the horizontal width is HoleHerr, and the vertical width is HoleVerr.

$$ErrCD = \frac{Hole_H err - Hole_H ref}{Hole_H ref} \times 100 \quad (7)$$

$$ErrCD = \frac{Hole_V err - Hole_V ref}{Hole_V ref} \times 100 \quad (8)$$

Figure 11B:
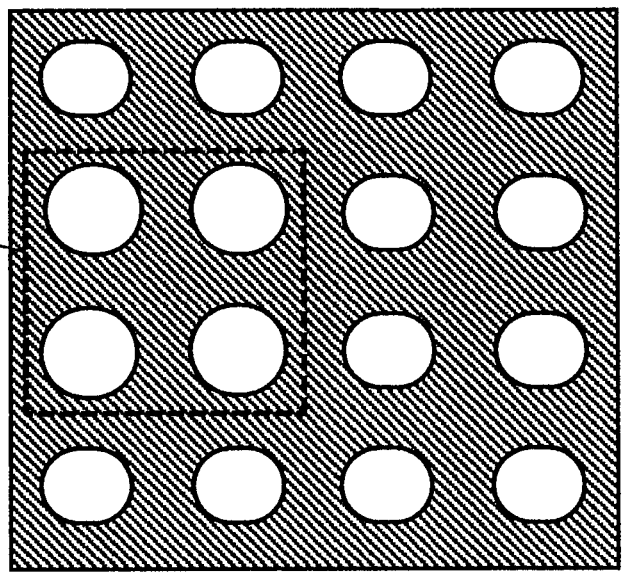
FIG. 11b is a wafer transfer image of the above mask.
Figure 11A:
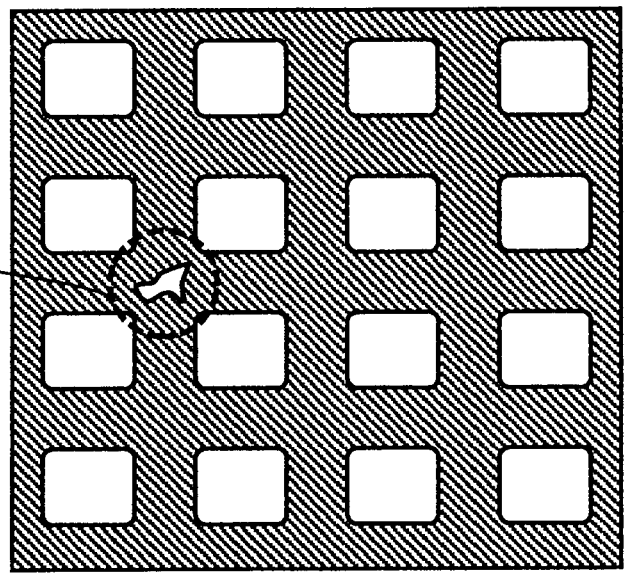
FIG. 11a is another example of a defect on a mask according to the present embodiment.

FIG. 11a illustrates another example of a defect on a mask where, in an area 6, there is a transmissive defect different from an original pattern. FIG. 11b illustrates an estimation image transferred to a wafer using the mask of FIG. 11a. Although the defect in the area 6 is not transferred as is in the estimation image, four patterns in the surrounding of the area 6, that is, the shape of the pattern in an area 7, is abnormal (expansion of a hole diameter).

As illustrated in the example of FIGS. 11a and 11b, when fluctuation of the line width and abnormality of the hole diameter which are identified as defects are seen at a plurality of portions in a wafer transfer estimation image due to one defect on the mask, it is preferable to display for reviewing, the shape of the most critical defect to make the operator make identification. In the present embodiment, reviewing is performed according to the following rule.

The following (1) to (3) are aligned in descending order of criticality of the defect. With (1), a review priority is the highest and, with (3), the review priority is the lowest.

(1) Detection of a defect on a mask and detection of a defect in a transfer estimation image mark high scores.

(2) Although detection of a defect on a mask is not critical, detection of a detect in a transfer estimation image marks a high score.

(3) Although detection of a defect on a mask marks a high score, detection of a defect in a transfer estimation image is not critical.

In the above, that "detection of a defect on a mask marks a high score" means that a calculation response value of an identification method determined in advance from a plurality of defect identification methods in a mask inspection apparatus is high. Generally, in case of a transmissive mask, a defect which is identified based on transmitted light is more likely to influence a transfer image than a defect which is identified based on reflected light. Further, a defect on a pattern edge is more likely to influence the transfer estimation image than an isolated defect. Taking these into account, a score of a mask defect is determined.

Further, that "detection of a defect in a transfer estimation image marks a high score" means that a measured error or error ratio of the line width or inter-line distance in case of a line pattern is great, or the measured error or error ratio of the hole diameter in the hole pattern is great.

Consequently, above (1) to (3) may be paraphrased respectively as follows.

(1) The degree of a defect which is identified in a first comparing unit is at or exceeding a third threshold, and the error ratio of the line width or inter-line distance of a defect corresponding to the above defect and identified in a second comparing unit is at or exceeding a fourth threshold;

(2) The degree of a defect identified in the first comparing unit is less than the third threshold, and the error ratio of the line width or inter-line width distance of a defect corresponding to the above defect and identified in the second comparing unit is at or exceeding a fourth threshold; and (3) The degree of a defect identified in the first comparing unit is at or exceeding the third threshold, and the error ratio of the line width or inter-line distance of a defect corresponding to the above defect and identified in the second comparing unit is less than the fourth threshold.

As stated above, "the degree of a defect" means the above-mentioned score determined for the defect identified in the first comparing unit. Further, the third threshold and the fourth threshold are respectively different reference values from the above first threshold and second threshold. In the present embodiment, appropriate values are determined individually for the first, second, third and fourth thresholds. The first threshold is a value which serves as a reference to identify a defect in a comparing circuit 108 which is the first comparing unit. The second threshold is a value which serves as a reference to identify a defect in a comparing circuit 301 which is the second comparing unit. The comparing circuit 301 can determine the review order using the third threshold and the fourth threshold. Further, the review device 500 can also determine the review order upon review by the operator.

Further, the degree of a defect can be classified into a plurality of scores using a plurality of thresholds. Similarly, the error ratio of the line width or inter-line distance of a defect can also be ranked using a plurality of thresholds. Further, based on these scores and ranks, it is possible to determine the review priority.

In the present embodiment, a defect is classified into one of (1) to (3). With (2), for example, although the size of a defect on a mask is small, there is a pattern near the defect, and therefore the hole diameter of the pattern in the transfer estimation image becomes large. Further, when there is a semi-transparent material adhering to a mask, it is difficult to detect this defect in the detection process using transmitted light or reflected light. However, in the transfer estimation image, the line width at a portion at which there is an adhering material changes, and this is detected as an obvious defect. This case is also classified as (2). By contrast with this, when there is a defect at a portion at which patterns do not concentrate, even if the size of the defect is large, this defect does not influence the other patterns and does not need to be repaired. This defect is classified as (3).

With a conventional method, (1) to (3) are not distinguished, and all defects are classified as (1). By contrast with this, in the present embodiment, with (2) taken into account, it is possible to ship more precise masks. Further, with (3) also taken into account, it is not necessary to perform repair. In addition, (2) and (3) require a transfer estimation image, and therefore the wafer image simulator 400 in FIG. 2 needs to perform simulation.

When a defect is detected on a mask by the inspection apparatus, and a transfer image of this mask on the wafer is estimated, there are cases where a defect is detected at a portion spaced a substantial distance apart from this defect. The review process for this defect in the transfer estimation image is skipped for the following reason.

Although the range of influence of one defect on the mask on the wafer transfer estimation image differs according to a technology node of this device and the type of pattern, the range is supposed to be about 10 μm to 20 μm at most. Therefore, when, in a wafer estimation image, a defect is produced in a pattern at a portion beyond the above range, another defect is predicted to be produced on a mask corresponding to this defect portion. Therefore, by setting a predetermined tolerance (search range) dimension and skipping review of a defect on a wafer transfer estimation image positioned spaced apart beyond this dimension, it is possible to reduce the number of defects which the operator needs to identify.

Further, when a test target is a hole pattern, the vertical and horizontal hole diameters are found in the transfer estimation image to calculate the measured error and error ratio. More specifically, by taking into account the figure density in the vertical direction and horizontal direction and the distance between adjacent patterns for patterns in the surrounds of the defect of interest, the direction in which the criticality is higher is determined. Next, the measured error or error ratio of the hole diameter in the direction which is determined to be important is preferentially pointed out to enable reviewing according to this priority.

In the example of FIG. 12, an interval Vpitch in the vertical direction of the hole pattern arranged in a matrix pattern is wider than an interval Hpitch in the horizontal direction. Hence, in this case, as for the influence of the defect on the hole pattern in the surrounding in the area 8, fluctuation of the dimension in the vertical direction is greater than fluctuation of the dimension in the horizontal direction. Consequently, in the review process, it is preferable to determine the review priority according to whether or not the measured error or error ratio in the horizontal direction exceeds a predetermined threshold (fourth threshold).

Thus, in the present embodiment, the greater value of the pattern density in one direction of the pattern and the pattern density in a direction vertical to this one direction is preferably reviewed preferentially.

FIG. 13 illustrates into which priority a defect is classified taking into account the criticality of the defect.

As illustrated in FIG. 13, a defect on the mask is first detected by the inspection apparatus (S101). Next, the transfer simulator is activated, and the transfer estimation image of a wafer is generated (S102). Further, at least one of the error ratio and the dimension error of the defect detected in S101 is calculated, and a score of the above defect is found according to whether or not the degree of the defect exceeds the third threshold (S103). Next, each pattern pitch in the horizontal direction and vertical direction is calculated for the transfer estimation image (S104).

The horizontal direction or vertical direction in which the criticality is higher is determined from the pattern pitch calculated in S104, and is set as a reviewing direction. Next, whether or not the error ratio in the preferential direction is at or exceeds a fourth threshold is determined (S105) and, when the error ratio is at or exceeds the fourth threshold, whether or not this defect is a significant defect in view of the score determined in S103 is determined (S106). That is, when the degree of the defect detected in S101 is at or exceeds the third threshold, the defect is identified as a significant defect and is classified as first priority (S107). The defect of the first priority is reviewed and repaired at all times.

In S106, the defect detected in S101 whose degree is determined to be less than the third threshold and is identified not to be a significant defect, is classified as second priority (S109). Although the defect of second priority is reviewed at all times, whether or not repair is necessary is determined based on a review result.

In S105, when the error ratio is determined not to be at or exceed a fourth threshold, whether or not the error ratio in a direction which is not a preferential direction is at or exceeds the fourth threshold, is then determined (S108). When the error ratio is at or exceeds the fourth threshold, the defect is classified as second priority irrespectively of the score of the defect (S109).

In S108, when the error ratio is determined not to be at or exceeding the fourth threshold, the dimension error in the horizontal direction and vertical direction is then determined (S110). Meanwhile, a fifth threshold which is different from any of the first, second, third and fourth thresholds can be used as a determination reference value. In S110, when the error is determined to be at or exceeding the fifth threshold, the defect is classified as second priority irrespectively of the score of the defect (S109).

In S110, when the error is determined not to be at or exceeding the fifth threshold, whether or not the defect is a significant defect in view of the score determined in S103 is determined (S111). That is, when the degree of the defect detected in S101 is at or exceeding the third threshold, the defect is identified to be a significant defect, in which case this defect is classified as third priority (S112). Although the defect of third priority is reviewed at all times, whether or not repair is necessary is determined based on the review result. By contrast with this, in S111, when the degree of the defect detected in S101 is determined to be less than the third threshold and the defect is identified not to be a significant defect, it is possible to skip reviewing of this defect (S113).

As described above, defect identification which is performed by estimating a transfer image on a wafer includes:
(1) identification of comparing a resist image generated from an optical image and a resist image generated from a reference image; and
(2) identification using a light intensity distribution image on a projection plane projected on a wafer simulating the exposure device.

According to the above methods (1) and (2), whether or not the defect on the mask is transferred to the wafer is estimated to identify the defect. As a result of estimation, if the defect is not transferred to the wafer, the defect on the mask is light, and it is determined that the defect need not be repaired. By contrast with this, the defect which is transferred to the wafer and causes abnormality may be repaired to improve the yield of manufactured masks.

Further, as a defect identification method, there is also a method of using a mask image estimated from an image acquired by a transmission optical system of the inspection apparatus and an image acquired by a reflection optical system of the inspection apparatus. This method is effective for ensuring quality of masks.

The features and advantages of the present invention may be summarized as follows.

The present invention provides a inspection apparatus and a inspecting method which can efficiently perform defect identification processing while estimating defects on a mask and the degree of influence of the defects on a wafer.

The present invention is not limited to the above-mentioned embodiments and may be utilized without departing from the spirit and scope of the present invention.

For example, a die-to-database inspecting system has been described mainly in the above embodiment where reference data generated from design pattern data used to manufacture masks and an actual pattern on the mask are compared. However, the present embodiment is applicable to a die-to-die inspecting system of comparing the same patterns of different chips in a mask when a plurality of chips are arranged which partially or entirely have the same pattern in the same mask. According to the die-to-die inspecting system, it is possible to generate an image (pseudo image) similar to an image of an actual mask acquired by a SEM microscope.

The above description of the Embodiment has not specified apparatus constructions, control methods, etc. which are not essential to the description of the invention, since any suitable apparatus constructions, control methods, etc. can be employed to implement the invention. Further, the scope of this invention encompasses all pattern inspection apparatuses and pattern inspection methods employing the elements of the invention and variations thereof which can be designed by those skilled in the art.

What is claimed is:

1. An inspection apparatus which determines whether or not there is a defect by irradiating light on to a sample on which a pattern is formed and forming an image of the sample on an image sensor by means of an optical system, the inspection apparatus comprising:
an optical image acquiring unit which acquires an optical image of the sample from the image sensor;
a first comparing unit which compares the optical image with a reference image which serves as a reference of the determination, and identifies a defect when a difference exceeds a first threshold;
a transfer image estimating unit which estimates a transfer image when patterns of the optical image of the sample and the reference image are transferred by a transfer device;
a second comparing unit which compares each of the transfer images and identifies a defect when a difference exceeds a second threshold; and
a review device which reviews information from the first comparing unit and the second comparing unit,
wherein the review device performs review in order of following (1) to (3):
(1) when the degree of a defect identified in the first comparing unit is a third threshold or above and an error ratio of a line width or an inter-line distance of a defect corresponding to the defect and identified in the second comparing unit is a fourth threshold or above;
(2) when the degree of a defect identified in the first comparing unit is less than the third threshold, and an error ratio of a line width or an inter-line distance of a defect corresponding to the defect and identified in the second comparing unit is the fourth threshold or above; and
(3) when the degree of a defect identified in the first comparing unit is the third threshold or above, and an error ratio of a line width or an inter-line distance of a defect corresponding to the defect and identified in the second comparing unit is less than the fourth threshold.

2. An inspection apparatus according to claim 1, wherein the review device reviews a defect within a predetermined dimension from a position of the transfer image corresponding to a position at which a defect is identified in the first comparing unit with the defect identified in the second comparing unit.

3. An inspection apparatus according to claim 1, wherein the review device preferentially reviews a greater value of a pattern density in one direction of the patterns and a pattern density in a direction vertical to the one direction.

4. An inspection method of determining whether or not there is a defect by irradiating light on to a sample on which a pattern is formed and forming an image of the sample on an image sensor by means of an optical system, the inspection method comprising:
acquiring an optical image of the sample from the image sensor;
comparing the optical image with a reference image which serves as a reference of the determination, and identifying a defect when a difference exceeds a first threshold;
estimating a transfer image of the optical image and a transfer image of the reference image;
comparing the transfer image of the optical image with the transfer image of the reference image and identifying a defect when a difference exceeds a second threshold; and
reviewing each of the transfer images in order of following (1) to (3):
(1) when the degree of a defect identified in the first comparing unit is a third threshold or above and an error ratio of a line width or an inter-line distance of a defect corresponding to the defect and identified in the second comparing unit is a fourth threshold or above;
(2) when the degree of a defect identified in the first comparing unit is less than the third threshold, and an error ratio of a line width or an inter-line distance of a defect corresponding to the defect and identified in the second comparing unit is the fourth threshold or above; and
(3) when the degree of a defect identified in the first comparing unit is the third threshold or above, and an error ratio of a line width or an inter-line distance of a defect corresponding to the defect and identified in the second comparing unit is less than the fourth threshold.

5. An inspection method according to claim 4, wherein the review device reviews a defect within a predetermined dimension from a position of the transfer image corresponding to a position at which a defect is identified in the first comparing unit with the defect identified in the second comparing unit.

6. An inspection method according to claim 4, wherein the review device preferentially reviews a greater value of a pattern density in one direction of the patterns and a pattern density in a direction vertical to the one direction.

* * * * *